United States Patent [19]

Malkin

[11] Patent Number: 5,847,141
[45] Date of Patent: Dec. 8, 1998

[54] PHOTOCHROMIC MATERIAL FOR ELECTRO-OPTIC STORAGE MEMORY

[75] Inventor: Jacob Malkin, Ashdod, Israel

[73] Assignee: Memory Devices, Inc., New York, N.Y.

[21] Appl. No.: 577,707

[22] Filed: Dec. 22, 1995

[51] Int. Cl.$^6$ ................................................ C07D 221/18
[52] U.S. Cl. ............................... 546/34; 524/90; 252/600
[58] Field of Search ................................ 546/34; 524/90; 252/600

[56] References Cited

U.S. PATENT DOCUMENTS

| | | | |
|---|---|---|---|
| 3,291,604 | 12/1966 | Michel et al. | 430/235 |
| 4,036,805 | 7/1977 | Tsujimoto et al. | 524/242 |
| 4,864,536 | 9/1989 | Lindmayer | 365/119 |
| 5,113,387 | 5/1992 | Goldsmith et al. | 369/44.38 |
| 5,177,227 | 1/1993 | Fischer et al. | 552/201 |
| 5,208,354 | 5/1993 | Fischer et al. | 552/200 |
| 5,268,862 | 12/1993 | Rentzepis | 365/151 |
| 5,407,885 | 4/1995 | Fischer et al. | 502/172 |

OTHER PUBLICATIONS

Article entitled Three–Dimensional Optical Storage Memory, D. A. Parthenopoulos & P. M. Rentzepis, *Science* 245, Aug. 25, 1989, pp. Reports 843–845.

Article entitled Experimental and Theoretical Study of Photoenolization Mechanism for 1–Methylanthraquinone, N. P. Gritsan, I. V. Khmelinski, and O. M. Usov, *J. Am. Chem. Soc.* 113, 1991, pp. 9615–9620.

Article entitled Photochemistry and Magnetochemistry, N. P. Gritsan et al., *Russian Journal of Physical Chemistry*, 64(11), 1990, pp. 1660–1663.

Book entitled *Organic Photochromes*, A. V. El'tsov, translated from Russian by Yu. E. Sviridov, 1990, Consultants Bureau, NY, pp. 257–260.

Article entitled Photochemistry of Molecular Systems for Optical 3D Storage Memory, J. Malkin et al., *Research on Chemical Intermediates* 19(2), 1993, pp. 159–189.

Article entitled Mechanism of Photochromic Transformations of Peri–Acyloxy–9,10–and 1,4–Anthraquinone Derivatives, N. P. Gritsan et al., unknown journal, hand numbered pp. 1–11.

Article entitled Photochromism and Kinetics of Naphthacenequinones, J. Malkin et al., *American Chemical Society*, 116(3), 1994, pp. 1101–1104.

Sokolyuk, N.T. et al, Russian Chemical Reviews, 1993, 62(11), pp. 1005–1024.

*Primary Examiner*—C. Warren Ivy
*Assistant Examiner*—Garth M. Dahlen
*Attorney, Agent, or Firm*—Wigman, Cohen, Leitner & Myers, P.C.

[57] ABSTRACT

The present invention relates to the field of photochromic material, in particular of photochromic compounds and matrices suitable for use in optical memory systems, including three dimensional optical memory systems for computers, multimedia applications and the like. The photochromic compounds have the following formula:

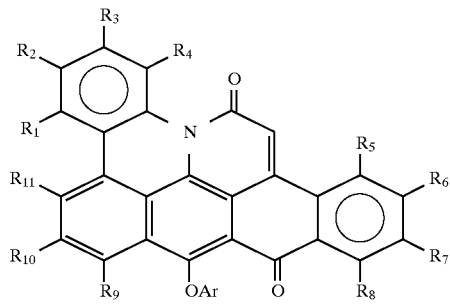

wherein the substituents are defined in the specification.

24 Claims, No Drawings

PHOTOCHROMIC MATERIAL FOR ELECTRO-OPTIC STORAGE MEMORY

FIELD OF THE INVENTION

The present invention relates to the field of photochromic material, in particular photochromic compounds and matrices suitable for use in optical memory systems, including three dimensional optical memory systems for computers, multimedia applications and the like.

BACKGROUND OF THE INVENTION

The need for improved memory devices, memory media and memory processing for computers has been dramatically demonstrated by the increasing speed and computational power of modern computer with vastly more complex programs to access and store in memory.

A major determinant of the size and price of computers is the memory. The data storage requirements of new high performance computers and multimedia applications of computers is very great, typically many gigabytes ($10^{12}$ bits) and even terabytes. New and improved, compact, low cost, very high capacity memory devices are needed. These memory devices should be able to store many gigabytes of information, and should randomly retrieve such information at the very fast random access speeds demanded by practical applications of modern computing and data processing.

An optical memory offers the possibility of packing binary-stated information into a storage medium at very high density, each binary bit occupying a space only about one wavelength in diameter. When practical limitations are taken into account this leads to a total capacity of about $10^{11}$ bits for a reasonably-sized two-dimensional optical storage medium.

In a two-dimensional memory, the theoretical storage density (proportional to $1/\lambda^2$ where $\lambda$ is two optical wave lengths) is $3.5 \times 10^8$ bits/cm$^2$ for $\lambda=532$ nm, whereas in a 3D memory the maximum storage density is $6.5 \times 10^{12}$ bits/cm$^3$ storage capacity for a given optical wave length. Although these values represent an upper limit to the storage capacity, the advantages of 3D data storage versus the current information storage media become apparent.

At the present two general classes of optical recording media exist, namely phase recording media and amplitude recording media. The first is based on light-induced changes of the index of refraction (i.e., phase holograms whereas the second refers to photo-induced changes in the absorption coefficient (i.e., hole burning) or two photon absorption processes.

Various optical memory devices have been proposed, including a three-dimensional optical memory described by Peter Rentzepis in U.S. Pat. No. 5,268,862, herein incorporated by reference, a three laser optical disk drive system described by Goldsmith et al. in U.S. Pat. No. 5,113,387, herein incorporated by reference and an optical memory system and method described by Lindmayer in U.S. Pat. No. 4,864,536, herein incorporated by reference. Another three-dimensional optical storage memory is described by Parthinopoulos et al. in *Science* Vol. 245, pages 843–845, August 1989, also herein incorporated by reference.

Generally, a photochromic material changes color when irradiated with UV, visible or infrared radiation while in the ground state. The light is absorbed by the ground state molecule, which then undergoes a photochemical reaction to form the metastable state. Preferably, the metastable state absorbs light at a different wavelength than the ground state molecule. The metastable state reverts to the ground state by thermal reversion or by being irradiated with light again, preferably light with a different wavelength than the light used to "read " the metastable state.

The photochromic material is incorporated within a three-dimensional matrix that is transparent to the activating light. The material is then irradiated, preferably by a laser, at points within the matrix to photochromically change the light absorption of the photochromic material at a site within the matrix. The 3D memory device "reads " the points by irradiating the sites with light at a wavelength for which the metastable state has a high absorptivity and fluorescence activity at that wavelength. The site is erased by irradiation with electromagnetic radiation at a frequency that will photochromically change the metastable state back to the ground state.

A variety of photochromic materials have been suggested for use as the changing element in optical memory systems. J. Malkin et al. in *Photochemistry of Molecular Systems for Optical 3D Storage Memory, Research on Chemical Intermediates*, Vol. 19, No. 2, pages 159–189 (1993) (herein incorporated by reference) suggests the use of spiropyrans as photochromic materials in 3D memories. Fisher et al., in U.S. Pat. Nos. 5,208,354; 5,177,2278 and 5,407,885, herein incorporated by reference, describe the synthesis and use of naphthacenequinones for the reversible optical storage of information.

The synthesis and use of naphthacenequinones as fluorescent dyes was described in U.S. Pat. No. 4,036,805, herein incorporated by reference; the kinetics of the photochromic effect were described by Malkin et al. in *Photochromism and Kinetics of Naphthacenequinones, Journal of the American Chemical Society*, Vol. 116, pages 1104–1105, 1994, herein incorporated by reference. The synthesis and properties of naphthacenequinones were reviewed by N. T. Sololyuk et al. in an article, *Naphthacenequinones: synthesis and properties, Russian Chemical Reviews*, 62(11) 1085–1024, 1993, herein incorporated by reference.

The photochromic transitions of antraquinones have also been studied in the following articles by N. P. Gritsan et al.: *Kinetic study of the Photochromic Transformations of 1-alkyl-9-10-antraquinones, Russian Journal of Physical Chemistry*, Vol. 64, 3081–3086, 1990; *Experimental and Theoretical Studies of Photoenolization Mechanisms for 1-methyl antraquinone, Journal of the American Chemical Society*, Vol. 113, pages 9915–9620, 1991; *and Mechanism of Photochromic Transformations of Peri-acyloxy-9,10-and 1,9-Antraquinone Derivatives, Journal of Photochemistry and Photobiology*, 1990A, Vol. 52, pages 137-; all of the above herein incorporated by reference.

A major problem with the use of the proposed naphthacenequinones and anthraquinones as the photochromic substrate in an optical three-dimensional memory is that the photoinduced form is not thermally stable and will revert to the ground state by itself. To prevent unwanted spontaneous reversion to the ground state, the matrix holding these photochromic materials must be cooled to at least −78° C. and preferably colder temperatures. Necessity in such low temperatures as a precondition for efficient functioning of devices utilizing above materials is associated with difficulties in design and limits the scope of possible applications.

Spiropyrans were proposed by Malkin et al. and Parthenopoulos et al. as possible photochromic materials for use in three-dimensional optical storage memory devices. However, spiropyrans have the following problems: the photoinduced state is not thermally stable, requiring the use of low temperatures; the use of low temperatures (about −78° C.) with spiropyrans dramatically decreases the quantum yield of the photoinduced reaction; and spiropyrans usually lose their photochromic properties after a few read-write-erase cycles.

OBJECTS AND ADVANTAGES OF THE INVENTION

A principle object of the present invention is to provide photochromic materials with the physical properties necessary for the use of these materials in practical 3-D memory storage devices.

Another object of the present invention is to provide photochromic materials of high capacity that are stable in use and reuse (read-write cycles) and can be used in optical memory at ambient temperature.

Another object of the present invention is to provide photochromic compounds that are thermally stable in the photoinduced state with a thermal back reaction rate constant of $1.6 \times 10^{-9}$ sec$^{-1}$ and lower.

Still another object of the present invention is to develop photochromic compounds with high absorptivity in the near UV region (extinction coefficients greater than $10^3 M^{-1} cm^{-1}$).

Yet another object of the present invention is to provide photochromic compounds with a quantum yield of the order of 0.15 and greater.

A still further object of the present invention is to provide photochromic compounds wherein the absorption of the colored form is in the visible region of the spectrum with high absorptivity and with a quantum yield of decoloration of the order of 0.001 and with the quantum yield of the photodestruction process which is less than 0.0001. The photodestruction process is the process whereby the photochromic material is destroyed by the write-read-erase process.

These and other objects of the present invention permit use of the photochromic compounds of the present invention in a transparent matrix that will not interfere with the desired properties of the photochromic compounds in optical memory devices to thereby avoid the problems of the prior art devices.

SUMMARY OF THE INVENTION

The photochromic compounds of the invention are thermally stable in the photoinduced state, are highly absorptive in the near UV state, have a good quantum yield of formation of the photoinduced metastable state, a low reaction rate of photodestruction, high absorption by the photoinduced metastable state in the visible spectrum and a good quantum yield on reversion from the photoinduced metastable state to the ground state.

Generally, the photochromic compounds of the invention are represented by Formula 1:

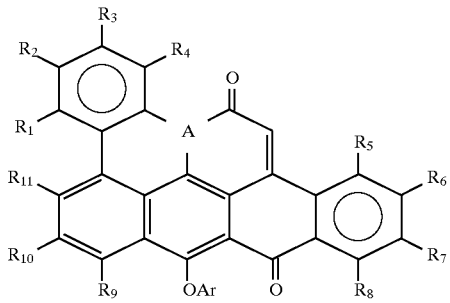

Formula 1 wherein A is N or CH; $R_1$ is independently chosen from H, n-alkyl, isoalkyl, alkyne, alkene, benzyl, halogen, perfluoroalkyl, O-alkyl, O-alkylene, O-isoalkyl, O-alkyne, O-phenyl, S-alkyl, S-alkene, S-alkyne, S-phenyl or S-benzyl; $R_2$ is independently chosen from H, n-alkyl, isoalkyl, alkyne, alkene, halogen, perfluoroalkyl, O-alkyl, O-alkylene, O-isoalkyl, O-alkyne, O-phenyl, O-benzyl, S-alkyl, S-alkene, S-alkyne, or S-phenyl; $R_3$ is independently chosen from H, n-alkyl, isoalkyl, alkyne, alkene, halogen, perfluoroalkyl, O-alkyl, O-alkylene, O-isoalkyl, O-alkyne, O-phenyl, O-benzyl, S-alkyl, S-alkene, S-alkyne, S-phenyl or S-benzyl; $R_4$ is independently chosen from H, alkyl, alkene, isoalkyl, alkyne, halogen or perfluoroalkyl; $R_5$ is independently chosen from H, alkyl, alkene, isoalkyl, alkyne, halogen or perfluoroalkyl; $R_6$ is independently chosen from H, n-alkyl, isoalkyl, alkene, alkyne, halogen, —OH, O-alkyl, O-alkylene, O-isoalkyl, O-alkyne, O-phenyl or O-benzyl, wherein the phenyl or benzyl group can have the following substituents: halogen, trifluoromethyl, alkyl, isoalkyl, —OH, O-alkyl or O-isoalkyl; $R_7$ is independently chosen from H, n-alkyl, isoalkyl, alkene, alkyne, halogen, —OH, O-alkyl, O-alkylene, O-isoalkyl, O-alkyne, O-phenyl or O-benzyl, wherein the phenyl or benzyl group can have the following substituents: halogen, trifluoromethyl, alkyl, isoalkyl, —OH, O-alkyl or O-isoalkyl; $R_8$ is independently chosen from H, trifluoromethyl, halogen, methyl, ethyl, propyl, isopropyl, butyl or isobutyl; $R_9$ is independently chosen from H, trifluoromethyl, halogen, methyl, ethyl, propyl, isopropyl, butyl or isobutyl; $R_{10}$ is independently chosen from H, n-alkyl, isoalkyl, alkene, alkyne, halogen, —OH, O-alkyl, O-alkylene, O-isoalkyl, O-alkyne, O-phenyl or O-benzyl, wherein the phenyl or benzyl group can have the following substituents: halogen, trifluoromethyl, alkyl, isoalkyl, —OH, O-alkyl or O-isoalkyl; $R_{11}$ is independently chosen from H, n-alkyl, isoalkyl, alkene, alkyne, halogen, —OH, O-alkyl, O-alkylene, O-isoalkyl, O-alkyne, O-phenyl or O-benzyl, wherein the phenyl or benzyl group can have the following substituents: halogen, trifluoromethyl, alkyl, isoalkyl, —OH, O-alkyl, or O-isoalkyl; and Ar is phenyl, 1-naphthyl, 2-naphthyl, alkyl substituted phenyl, halogen substituted phenyl, perfluroalkyl substituted phenyl, alkyl substituted-1-naphthyl, halogen substituted-1-naphthyl, perfluoroalkyl substituted 1-naphthyl, alkyl substituted-2-naphthyl, halogen substituted-2-naphthyl or perfluoroalkyl substituted-2-naphthyl.

Preferred are compounds wherein $R_1$ is H, $R_2$ is O-alkyl or n-alkyl, $R_3$ through $R_{11}$ is H, A is nitrogen and Ar is phenyl. Especially preferred compounds are compounds wherein $R_1$ is H or $CH_3O$, and $R_2$ is $O-CH_3$ trifluoromethyl, isopropyl, n-hexyl, halogen (especially chloro) or n-butyl, $R_3$ through $R_{11}$ is H, A is nitrogen and Ar is phenyl.

DETAILED DESCRIPTION OF THE INVENTION

A. Method of Making the Matrix

A number of different photochromic compounds of the invention (also referred to herein as "naphthacene pyridones") are derived from the naphthacenepyridone nucleus and the naphthacenequinone nucleus. The photochromic compounds of the invention can be used to form the photochromic matrix that serves as the memory storage device in a variety of ways. One method of fabricating a photochromic matrix is to dissolve the photochromic material in a polymer that is transparent at least at the following light frequencies: the frequency used to form the metastable state, the frequency used to "read" the metastable state and the frequencies used to transform the metastable state back to the ground state. Examples of suitable polymers are polymethylmethacrylate, polystyrene, polyvinyl alcohol. These polymers are known to those skilled in the art and further it will be shown how the present invention can be implemented with these polymers. The incorporation of the photochromic compounds of the invention into the polymers is accomplished by known methods, for example, by dissolving the polymer and photochromic compounds in solvent and then removing the solvent, calendaring or extrusion.

The following photochromatic compounds are considered as being within the scope of the invention:

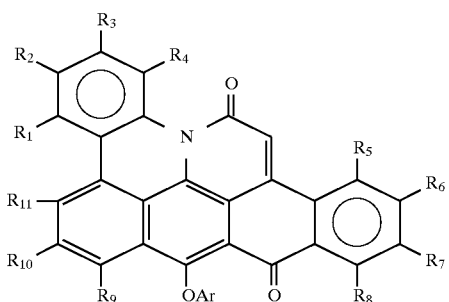

Formula 2

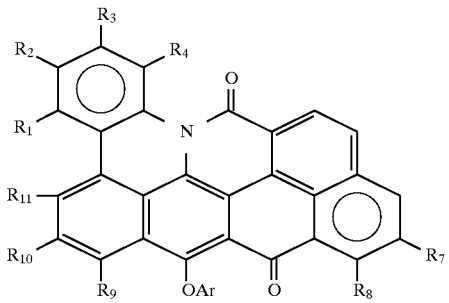

Formula 3a

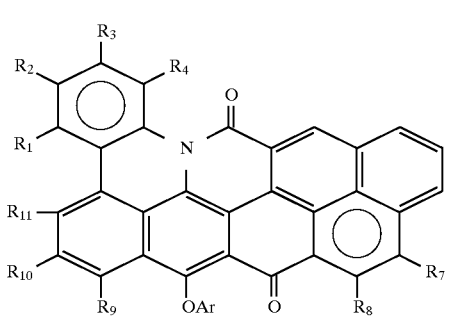

Formula 3b

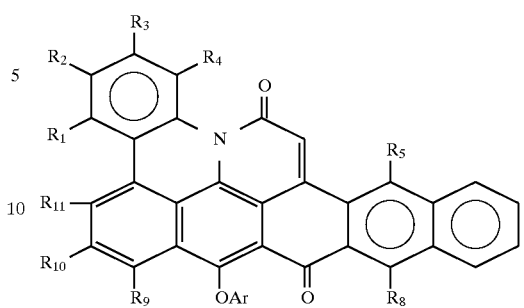

Formula 4a

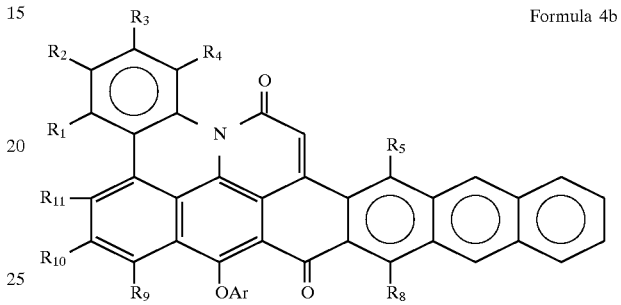

Formula 4b

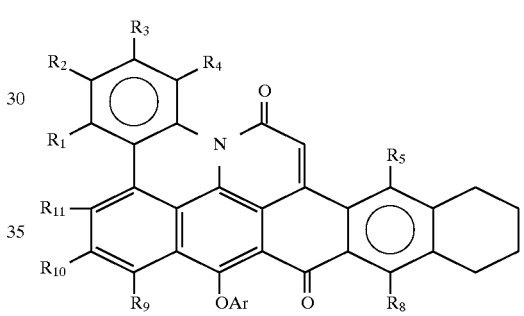

Formula 4c

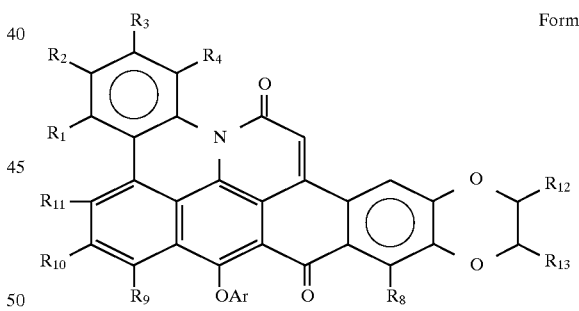

Formula 5

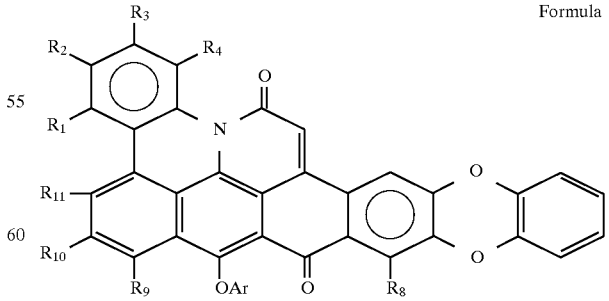

Formula 6

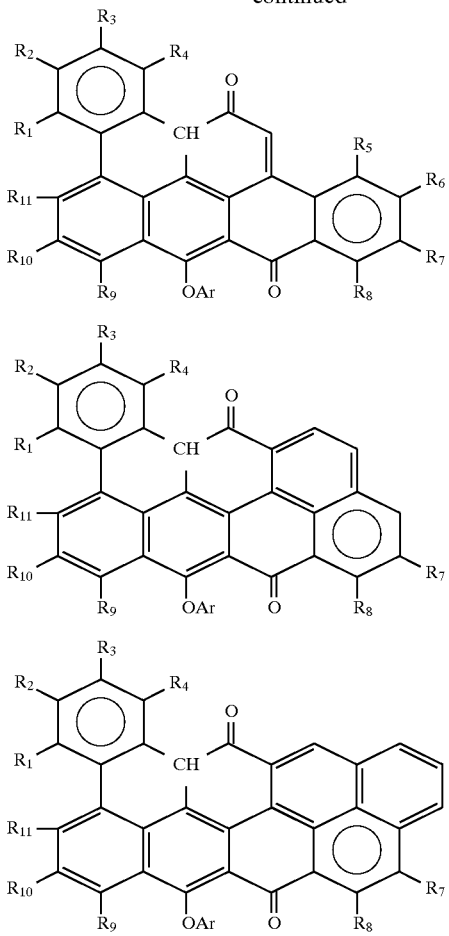

Formula 7

Formula 8a

Formula 8b

The Formulae 2-8 are independently substituted with substituents represented by $R_1$–$R_{13}$. The substituents for $R_1$ through $R_{13}$ are given below with substituents as follows, wherein $R_1$ is independently selected from H, n-alkyl, isoalkyl, alkyne, alkene, benzyl, halogen, perfluoroalkyl, O-alkyl, O-alkylene, O-isoalkyl, O-alkyne, O-phenyl, S-alkyl, S-alkene, S-alkyne, S-phenyl or S-benzyl; $R_2$ is independently selected from H, n-alkyl, isoalkyl, alkyne, alkene, halogen, perfluoroalkyl, O-alkyl, O-alkylene, O-isoalkyl, O-alkyne, O-phenyl, O-benzyl, S-alkyl, S-alkene, S-alkyne, or S-phenyl; $R_3$ is independently selected from H, n-alkyl, isoalkyl, alkyne, alkene, halogen, perfluoroalkyl, O-alkyl, O-alkylene, O-isoalkyl, O-alkyne, O-phenyl, O-benzyl, S-alkyl, S-alkene, S-alkyne, S-phenyl or S-benzyl; $R_4$ is independently selected from H, alkyl, alkene, isoalkyl, alkyne, halogen or perfluoroalkyl; $R_5$ is independently selected from H, alkyl, alkene, isoalkyl, alkyne, halogen or perfluoroalkyl; $R_6$ is independently selected from H, n-alkyl, isoalkyl, alkene, alkyne, halogen, —OH, O-alkyl, O-alkylene, O-isoalkyl, O-alkyne, O-phenyl or O-benzyl, wherein the phenyl or benzyl group can have the following substituents: halogen, trifluoromethyl, alkyl, isoalkyl, —OH, O-alkyl or O-isoalkyl; $R_7$ is independently selected from H, n-alkyl, isoalkyl, alkene, alkyne, halogen, —OH, O-alkyl, O-alkylene, O-isoalkyl, O-alkyne, O-phenyl or O-benzyl, wherein the phenyl or benzyl group can have the following substituents: halogen, trifluoromethyl, alkyl, isoalkyl, —OH, O-alkyl or O-isoalkyl; $R_8$ is independently selected from H, trifluoromethyl, halogen, methyl, ethyl, propyl, isopropyl, butyl or isobutyl; $R_9$ is independently selected from H, trifluoromethyl, halogen, methyl, ethyl, propyl, isopropyl, butyl or isobutyl; $R_{10}$ is independently selected from H, n-alkyl, isoalkyl, alkene, alkyne, halogen, —OH, O-alkyl, O-alkylene, O-isoalkyl, O-alkyne, O-phenyl or O-benzyl, wherein the phenyl or benzyl group can have the following substituents: halogen, trifluoromethyl, alkyl, isoalkyl, —OH, O-alkyl or O-isoalkyl; $R_{11}$, is independently selected from H, n-alkyl, isoalkyl, alkene, alkyne, halogen, —OH, O-alkyl, O-alkylene, O-isoalkyl, O-alkyne, O-phenyl or O-benzyl, wherein the phenyl or benzyl group can have the following substituents: halogen, trifluoromethyl, alkyl, isoalkyl, —OH—O-alkyl or O-isoalkyl; and Ar is phenyl, 1-naphthyl, 2-naphthyl, alkyl substituted phenyl, halogen substituted phenyl, perfluroalkyl substituted phenyl, alkyl substituted-1-naphthyl, halogen substituted-1-naphthyl, perfluoroalkyl substituted 1-naphthyl, alkyl substituted-2-naphthyl, halogen substituted-2-naphthyl or perfluoroalkyl substituted-2-naphthyl; and wherein $R_{12}$ and $R_{13}$ are independently selected from H, n-alkyl, carboxylic acid and carboxylic esters.

Preferred are compounds wherein $R_1$ is H, $R_2$ is O-alkyl or n-alkyl, $R_3$ through $R_{11}$ is H, A is nitrogen and Ar is phenyl. Especially preferred compounds are compounds wherein $R_1$ is H or $CH_3O$, and $R_2$ is $O—CH_3$ trifluoromethyl, isopropyl, n-hexyl, halogen (especially chloro) or n-butyl, $R_3$ through $R_{11}$ is H, A is nitrogen and Ar is phenyl.

B. Method of Making Preferred Compounds

Compounds of Formulas 4a, 4b, 4c, 5 and 6 can generally be synthesized by substituting the following compounds for the substituted phthalic anhydrides.

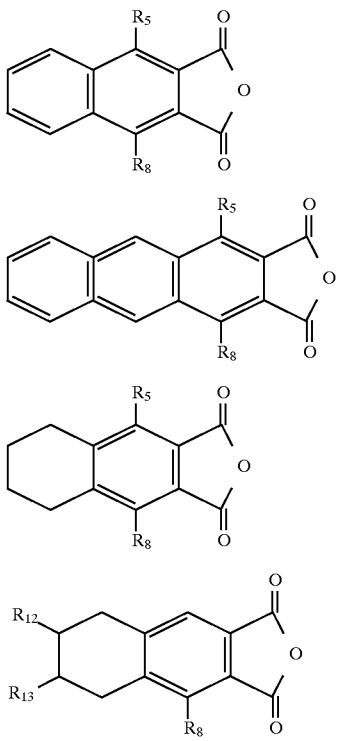

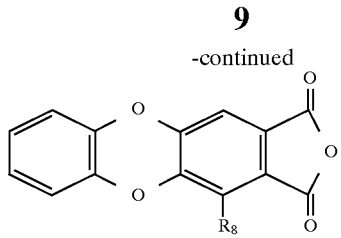

The substituted anhydrides are reacted with suitably substitute 1-(N-chloroacetyl amino-4O-phenyl-8-phenyl naphthalene in the presence of aluminum trichloride followed by cyclization with methylsulfuric acid in benzene with azetropic removal of water, forming the 6-amino naphthacenequinone. The 6 amino naphthacenequinone is cyclized by heating in pyridone at about 450° C. forming the respective naphtha-dione, which is reduced with hydracine from compounds of formulas 4a, 4b, 4c, 5 and 6.

For the compounds and formulas 4a, 4b, 4c, 5 and 6, the substituent $R_1$–$R_3$ are independently selected with $R_1$ and $R_2$ are independently selected from H, alkyl, O-isoalkyl, isoalkyl, O-isoalkyl, halogen and $CF_3$, $R_3$, $R_4$, $R_5$, $R_8$, $R_9$, $R_{10}$ and $R_{11}$ are H and $R_{12}$ and $R_{13}$ are selected from H and $CH_3$.

Best Mode (Synthesis)

EXAMPLE 1

Synthesis of 5,14-Diketo,6-phenoxy,11-butyl-13a-aza-5,14,15h-phenanthreno[7,8,9,10-ponh]naphthacene (further referred to as CM-X1):

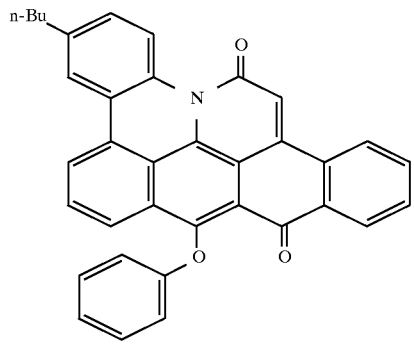

CM-X1

Initial 9-phenoxy-N-p-butylphenylnaphthacenopyridone (further referred to as I) was synthesized by heating of known compound N-chloroacetyl-6-N-p-butylphenylamino-11-5,12-naphthacenequinone (further referred to as III) in a 3% alcohol solution of sodium hydroxide (as described by Yu. Gerasimenko and N. T. Poteleshenko: Bull.Acad.Sci. of the USSR, 1982, 18, 899, herein incorporated by reference): A mixture of 3 g of compound III, 3 g of anhydrous sodium carbonate and 30 g of phenol was stirred at 186° C. for 3 h, cooled, diluted with methanol and filtered. The product was washed with methanol and dried. The precipitate was dissolved in a 5:1 mixture of chloroform and ethyl acetate and chromatographed on silica gel

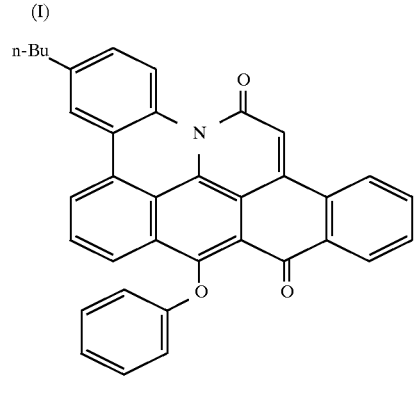

CM-X1

CM-X1 was synthesized by irradiation of $CH_2Cl_2$ solution of compound 9-phenoxy-N-p-butylphenylnaphthacenopyridone (I) in the presence of I2 and in the absence of air: 0.02 g I in 150 ml $CH_2Cl_2$ were irradiated under stirring in the presence of 20 mg of I2 for 8 hours by full light of tungsten lamp (100 W). With cooling, the reaction mixture is poured into water and is stirred. The precipitate is isolated by filtration, washed with water and dried. Chromatography with copious methylene chloride over silica gel gives 0.01 g CM-X1 (5,14-Diketo,6-phenoxy,11-butyl-13a-aza-5,14,15h-phenanthreno[7,8,9,10-ponh]naphthacene). CM-X1 was obtained in the form of yellow needles melting 254° C. (from toluene). M 526. Found H 5.03 N 2.40 C 83.20 $C_{36}H_{25}NO_3$. Calculated % H 4.85 C 83.22 N 2.70 O 9.24. The following $\lambda_{max}$ values are obtained (UV/VIS spectrum, in $CH_2Cl_2$): 420, 453 and 490 nm.

The physical properties of the synthesized compound CM-X1 are as follows: specific gravity $d_{20}$=1.36, soluble in toluene, chloroform and ethanol. The luminescent properties are as follows: energy of singlet state $E_S$=242 kJ/mol; energy of triplet state $E_T$=261 kJ/mol; quantum yield of triplet state $\Phi_T$=0.40; lifetime of triplet state $\tau_T$=0.12 msec; lifetime of singlet state $\tau_S$<0.2 nsec; quantum yield of photocoloration $\Phi_B$=0.36 (for wavelength of 405 nm).

EXAMPLE 2

CM-X2 was synthesized using the same procedure:

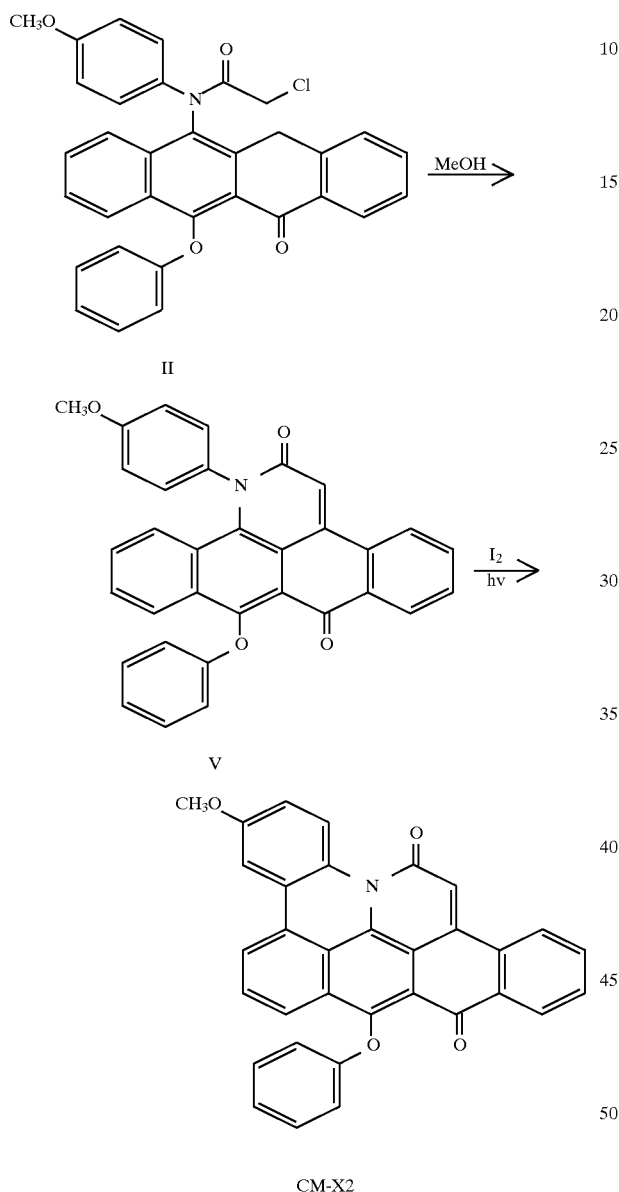

CM-X2

5,14-Diketo,6-phenoxy,11-methoxy-13a-aza-5,14,15h-phenanthreno[7,8,9,10-ponh]naphthacene designated further as CM-X2 was obtained in the form of yellow needles melting 254° C. (from toluene). M 493.5 $C_{33}H_{19}NO_4$ Found H 4.03 N 2.80 C 81.20 Calculated % H 3.85 C 80.2 N 2.83 O 12.96. The following $\lambda_{max}$ values are obtained (UV/VIS spectrum, in $CH_2Cl_2$): 414, 449 and 485 nm.

The initial 9-phenoxy-N-p-anisylnaphthacenopyridone (further referred to as V) was synthesized by heating N-chloroacetyl-6-N-p-anisylamino-11-phenoxy-5,12-naphthacenequionone (further referred to as II) in a 3% alcohol solution of sodium hydroxide (as described by Yu. Gerasimenko and N. T. Poteleshenko: *Bull.Acad.Sci. of the USSR*, 1982, 18, 899): A mixture of 3 g of compound III, 3 g of anhydrous sodium carbonate and 30 g of phenol was stirred at 186° C. for 3 h, cooled, diluted with methanol and filtered. The product was washed with methanol and dried. The precipitate was dissolved in a 5:1 mixture of chloroform and ethyl acetate and chromatographed on silica gel.

Physical properties of the synthesized compound are as follows: specific gravity $d_{20}$=1.30, soluble in toluene, chloroform and ethanol. The luminescence properties are as follows: Energy of singlet state $E_S$=281 kJ/mol, Energy of triplet state $E_T$=250 kJ/mol, quantum yield of triplet state $\Phi_T$=0.61, lifetime for triple state $\tau_T$=0.42 msec, lifetime of singlet state $\tau_S$<0.2 msec, quantum yield of photocoloration $\Phi_B$=0.45 (at 405 nm).

EXAMPLE 3

CM-X3 was synthesized using the same procedure:

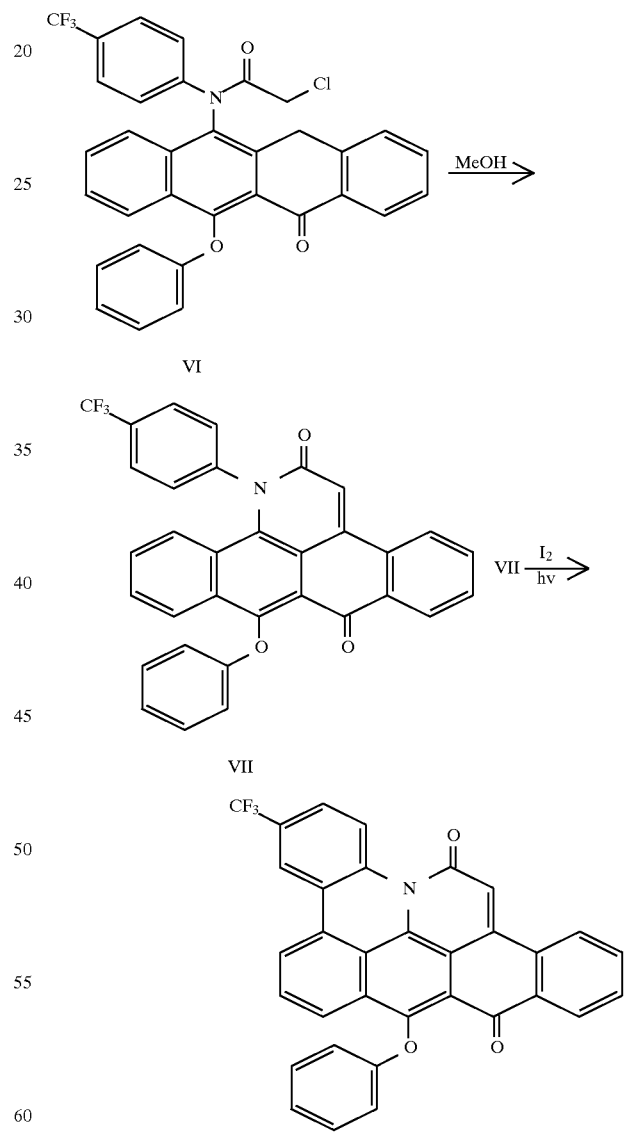

CM-X3

5,14-Diketo,6-phenoxy,11-trifluoromethyl-13a-aza-5,14,15h-phenanthreno[7,8,9,10-ponh]naphthacene designated further as CM-X3 was obtained in the form of yellow needles melting 261° C. (from toluene). M 531 C$_{33}$H$_{16}$NO$_3$F$_3$ Found H 3.03 N 2.60 C 74.20 O 8.9 Calculated % H 3.01 C 74.6 N 2.63 O 9.03 F 10.73. The following $\lambda_{max}$ values are obtained (UV/VIS spectrum, in CH$_2$Cl$_2$): 414, 449 and 485 nm.

The initial 9-phenoxy-N-p-trifluoromethylphenylnaphthacenopyridone was synthesized by heating N-chloroacetyl-6-N-p-trifluoromethylphenylamino-11-phenoxy-5,12-naphthacenequionone VI in a 3% alcohol solution of sodium hydroxide: A mixture of 5 g of compound N-chloroacetyl-6-N-p-trifluoromethylphenylamino-11-phenoxy-5,12-naphthacenequionone VII, 5 g of anhydrous sodium carbonate and 42 g of phenol was stirred at 186° C. for 2 h, cooled, diluted with methanol and filtered. The product was washed with methanol and dried. The precipitate was dissolved in ethyl acetate and chromatographed on silica gel.

EXAMPLE 4

CM-X4 was synthesized using the same procedure:

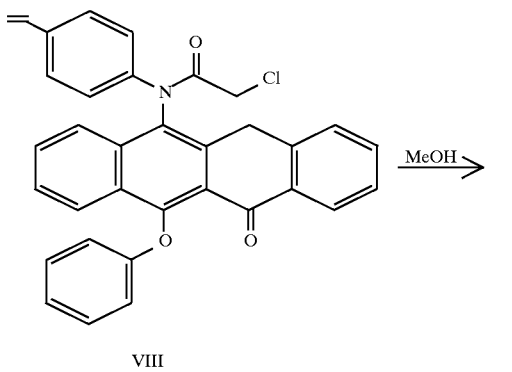

VIII

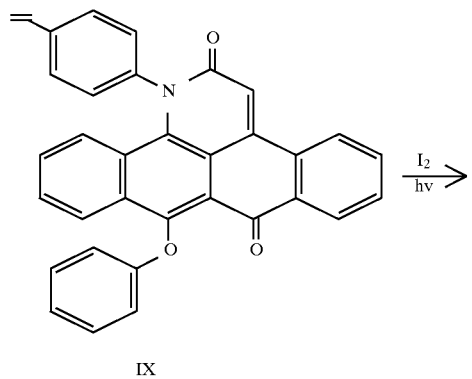

IX

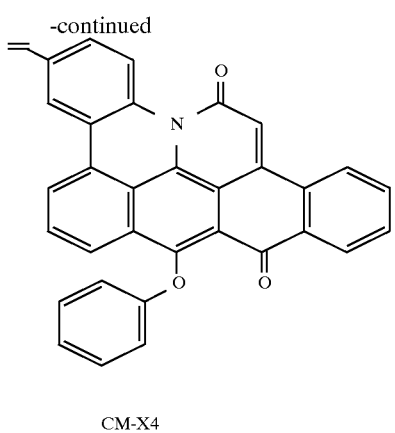

CM-X4

5,14-Diketo,6-phenoxy,11-vinyl-13a-aza-5,14,15h-phenanthreno[7,8,9,10-ponh]naphthacene designated further as CM-X4 was obtained in the form of yellow crystalles melting 231° C. (from toluene). M 489.5 C$_{34}$H$_{19}$NO$_3$ Found H 3.90 N 2.40 C 83.20 O 8.73 Calculated % H 3.88 C 83.3 N 2.86 O 9.80. The following $\lambda_{max}$ values are obtained (UV/VIS spectrum, in CH$_2$Cl$_2$): 414, 449 and 485 nm.

The initial 9-phenoxy-N-p-vinylphenylnaphthacenopyridone IX was synthesized by heating N-chloroacetyl-6-N-p-vinylphenylamino-11-phenoxy-5,12-naphthacenequinone VIII in a 3% alcohol solution of sodium hydroxide: A mixture of 2.5 g of N-chloroacetyl-6-N-p-vinylphenylamino-11-phenoxy-5,12-naphthacenequinone, 2.5 g of anhydrous sodium carbonate and 25 g of phenol was stirred at 186° C. for 4 h, cooled, diluted with methanol and filtered. The product was washed with methanol and dried. The precipitate was dissolved in ethyl acetate and chromatographed on silica gel.

EXAMPLE 5

Starting 9-phenoxy-N-p-isopropoxyphenylnaphthacenopyridone (further referred to as XI) was synthesized by heating N-chloroacetyl-6-N-p-isopropxyphenylamino-11-phenoxy-5,12-naphthacenequinone (further referred to as X) in a 3% alcohol solution of sodium hydroxide (as described by Yu. Gerasimenko and N. T. Poteleshenko: *Bull.Acad.Sci. of the USSR,* 1982, 18, 899): A mixture of 6 g of N-chloroacetyl-6-N-p-isopropxyphenylamino-11-phenoxy-5,12-naphthacenequinone,6 g of anhydrous sodium carbonate and 30 g of phenol was stirred at 186° C. for 3 h, colled, diluted with methanol and filtered. The product was washed with methanol and dried. The precipitate was dissolved in a 5:1 mixture of chloroform and ethyl acetate and chromatographed on silica gel.

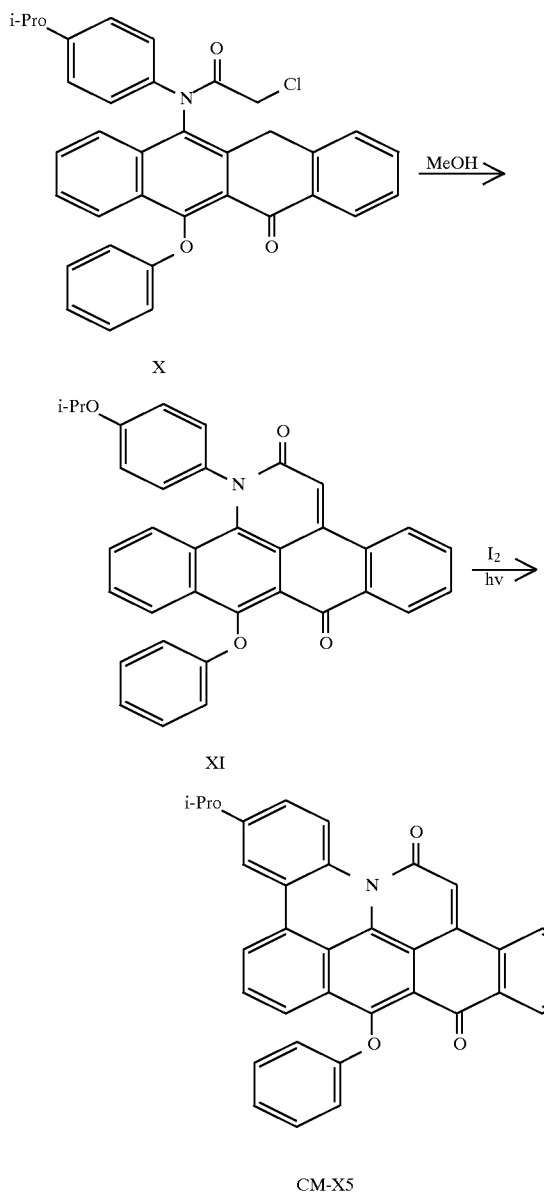

CM-X5

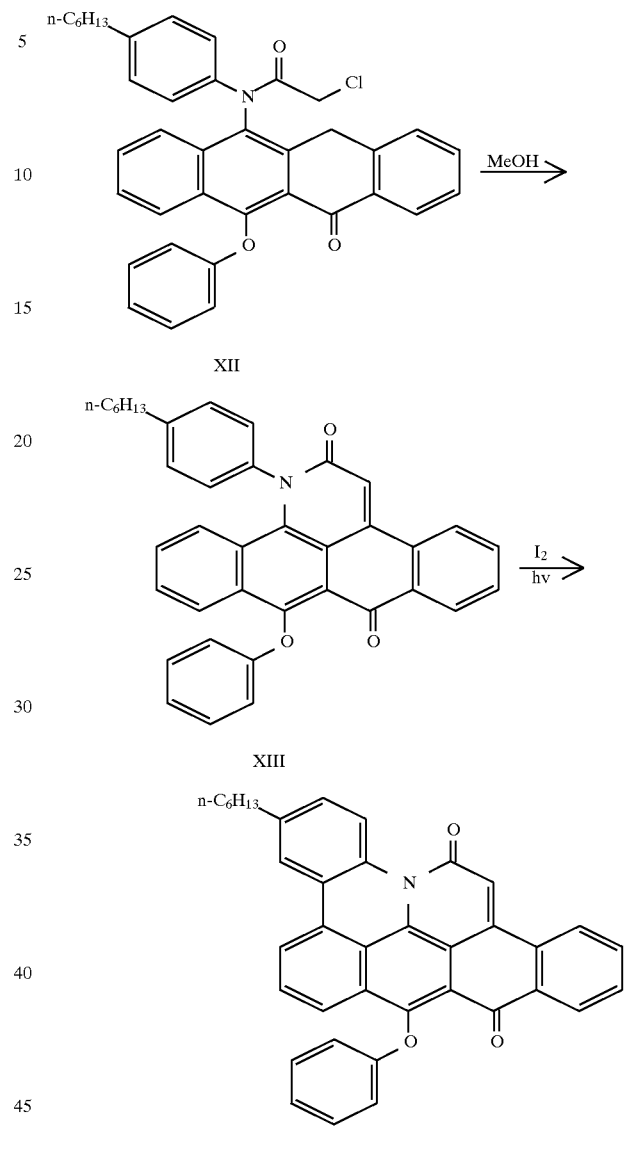

EXAMPLE 6
CM-X6 was synthesized using the following procedure:

CM-X6

CM-X5 was synthesized by irradiation of $CH_2Cl_2$ solution of compound 9-phenoxy-N-p-isopropoxyphenylnaphthacenopyridone in the presence of $I_2$: 0.02 g 9-phenoxy-N-p-isopropoxyphenylnaphthacenopyridone in 150 ml $CH_2Cl_2$ were irradiated under stirring in the presence of 20 mg of $I_2$ for 8 hours by full light of tungsten lamp (100 W). With cooling, the reaction mixture is poured into water and is stirred. The precipitate is isolated by filtration, washed with water and dried. Chromatography with copious methylene chloride over silica gel gives 0.01 g CM-X5 (5,14-Diketo, 6-phenoxy,11-isopropoxy-13a-aza-5,14,15h-phenanthreno[7,8,9,10-ponh]naphthacene). CM-X5 was obtained in the form of yellow needles melting 254° C. (from toluene). M 521.5 Found H 4.3 N 2.31 C 80.5 O 12.0. $C_{35}H_{23}NO_4$. Calculated % H 4.41 N 2.68 C 80.53 O 12.27. The following $\lambda_{max}$ values are obtained (UV/VIS spectrum, in $CH_2Cl_2$): 420, 453 and 490 nm.

5,14-Diketo,6-phenoxy,11-n-hexyl-13a-aza-5,14,15h-phenanthreno[7,8,9,10-ponh]naphthacene designated further as CM-X6 was obtained in the form of yellow needles melting 254° C. (from toluene). M 548 $C_{38}H_{29}NO_3$ Found H 5.2 N 2.60 C 83.0 O 8.9. Calculated % H 5.29 C 83.21 N 2.55 O 8.76. The following $\lambda_{max}$ values are obtained (UV/VIS spectrum, in $CH_2Cl_2$): 411, 449 and 496 nm.

The starting 9-phenoxy-N-p-hexylnaphthacenopyridone XIII was synthesized by heating N-chloroacetyl-6-N-p-hexylphenylamino-11-phenoxy-5,12-naphthacenequinone XII in a 3% alcohol solution of sodium hydroxide (as described by Yu. Gerasimenko and N. T. Poteleshenko: Bull.Acad.Sci. of the USSR, 1982, 18, 899): A mixture of 3 g of N-chloroacetyl-6-N-p-hexylphenylamino-11-phenoxy-5,12-naphthacenequinone, 3 g of anhydrous sodium carbonate and 30 g of phenol was stirred at 186° C. for 3 h, cooled, diluted with methanol and filtered. The product was washed with methanol and dried. The precipitate was dissolved in a 5:1 mixture of chloroform and ethyl acetate and chromatographed on silica gel.

EXAMPLE 7

CM-X7 was synthesized using the following procedure:

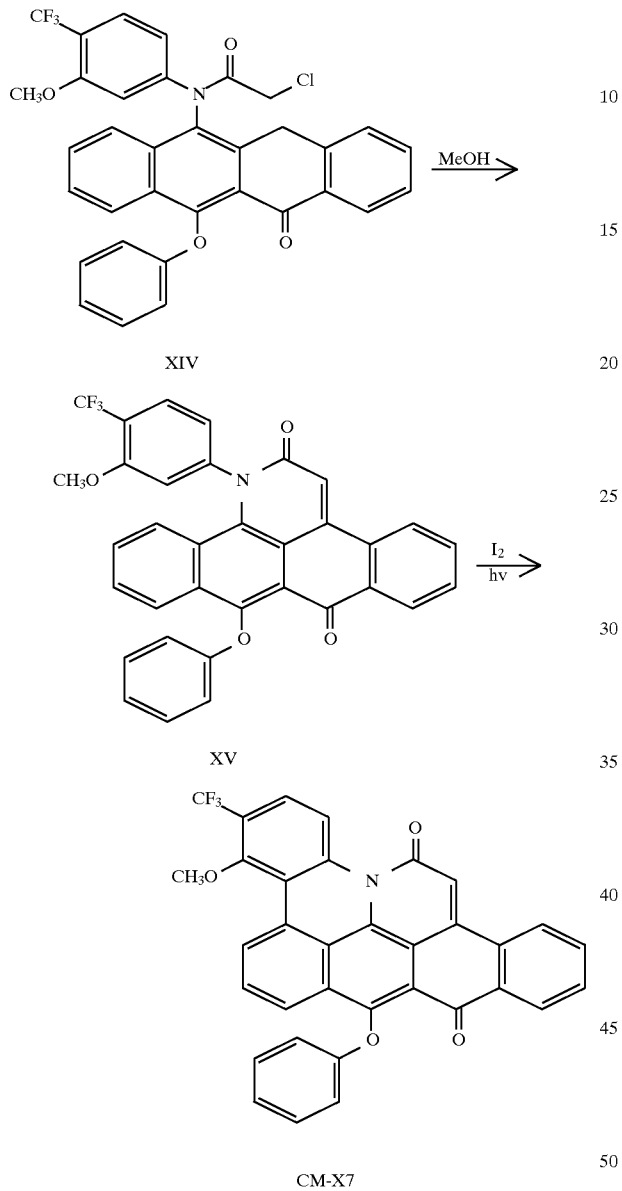

CM-X7

5,14-Diketo,6-phenoxy,10-methoxy,11-trifluoromethyl-13a-aza-5,14,15h-phenanthreno[7,8,9,10-ponh]naphthacene CM-X7 was obtained in the form of needles melting 277° C. (from ethanol). M 561 $C_{34}H_{18}NO_4F_3$ Found H 3.1 N 2.60 C 73.1 O 11.0 F 10.5 Calculated % H 3.20 C 72.7 N 2.5 O 11.4 F 10.2. The following $\lambda_{max}$ values are obtained (UV/VIS spectrum, in $CH_2Cl_2$): 414, 446 and 480 nm.

The initial 9-phenoxy-N-p-trifluoromethyl-o-methoxyphenylnaphthacenopyridone (referred to as XV) was synthesized by heating N-chloroacetyl-6-N-p-trifluoromethyl-o-methoxyphenyl-amino-11-phenoxy-5,12-naphthacenequinone XIV in a 3% alcohol solution hydroxide (as described by Yu. Gerasimenko and N. T. Poteleshenko: Bull.Acad.Sci. of the USSR, 1982, 18, 899): A mixture of 3 g of compound N-chloroacetyl-6-N-p-trifluoromethyl-o-methoxyphenylamino-11-phenoxy-5,12-naphthacenequinone, 3 g of anhydrous sodium carbonate and 30 g of phenol was stirred at 186° C. for 3 h, cooled, diluted with methanol and filtered. The product was washed with methanol and dried. The precipitate was dissolved in a 5:1 mixture of chloroform and ethyl acetate and chromatographed on silica gel.

EXAMPLE 8

CM-X8 was synthesized using the following procedure:

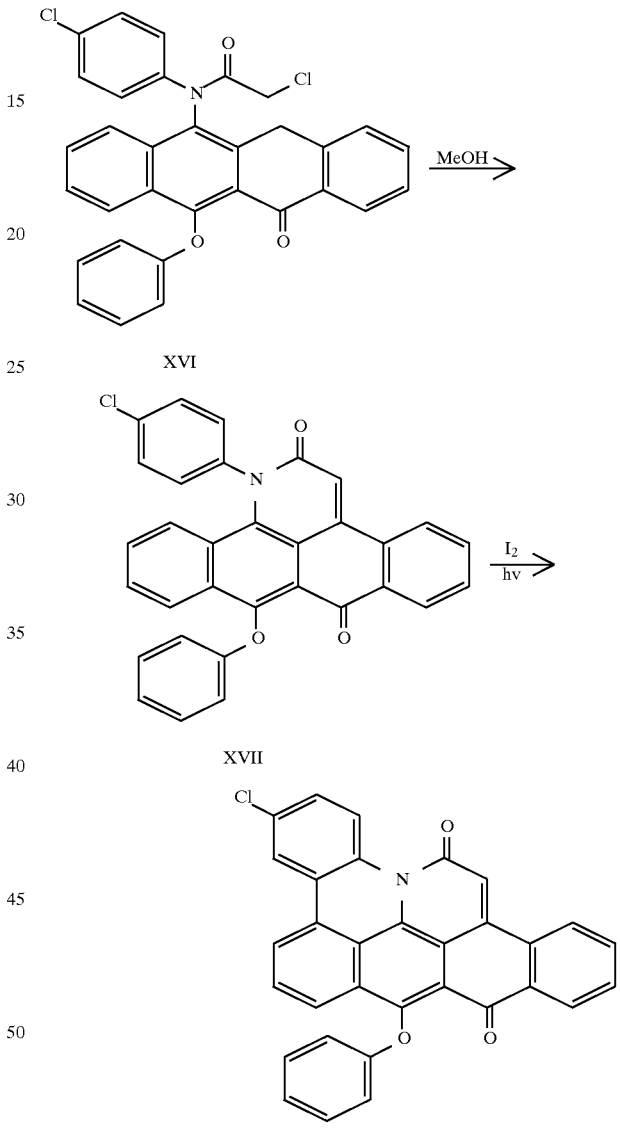

CM-X8

5,14-Diketo,6-phenoxy,11-chloro-13a-aza-5,14,15h-phenanthreno[7,8,9,10-ponh]naphthacene designated further as CM-X8 was obtained in the form of yellow needles melting 267° C. (from toluene). M 498 $C_{32}H_{16}NO_3Cl$ Calculated % H 6.42 C 77.1 N 2.81 O 9.6 Cl 7.1. The following $\lambda_{max}$ values are obtained (UV/VIS spectrum, in $CH_2Cl_2$): 414, 453 and 491 nm.

The initial 9-phenoxy-N-p-chlorophenylnaphthacenopyridone (further referred to as XVIII) was synthesized by heating N-chloroacetyl--N-p- chlorophenylamino-11-phenoxy-5,12-naphthacenequinone XVII in a 3% alcohol solution of sodium hydroxide (as described by Yu. Gerasimenko and N. T. Poteleshenko: *Bull.Acad.Sci. of the USSR,* 1982, 18, 899): A mixture of 4.5 g of N-chloroacetyl-6-N-p-chlorophenylamino-11-phenoxy-5,12-naphthacenequinone, 4.5 g of anhydrous sodium carbonate and 50 g of phenol was stirred at 186° C. for 5.5 h, cooled, diluted with methanol and filtered. The product was washed with methanol and dried. The precipitate was dissolved in a 5:1 mixture of chloroform and ethyl acetate and chromatographed on silica gel.

Formation of a Photochromic Matrix

The photochromic matrix was prepared by the polymerization of liquid methylmethacrylate solution and photochromic compound.

EXAMPLE 1

20 ml of a $10^{-3}$ M solution of CM-X4 in methylmethacrylate was polymerized in the presence of 2 mg of bis(azodiisobutyronitrile). The solution was left standing for more than 30 hours at 40° C. The polymer can be machined and buffed to form a desired shape for use as an optical memory.

The 2 photon writing can be carried out with the light having, for instance, a wavelength 532 nm or 532 and 1064 nm. Reading can be carried out with the light 532 nm (one photon reading) or 1064 nm (2 photon reading). However both writing and reading can be carried out by means of wavelengths which differ from the above values. This is true provided that the energy of two photon absorption exceed the required threshold. For instance the two photon absorption was implemented by two photon with the wavelength 632 nm. The two photon absorption is expedient to carry with either femtosecond (say 100 fs) or short pulse picosecond laser. One photon reading can be also realized with the light having any other wavelength within absorption spectra of the form B (450–600 nm).

Comparative characteristics of the photoinduced form B of CM-X1, CM-X2 and naphthacenequinone (R)

(Data for prior art from reference J. Malkin et. al Journal of the American Chemical Society, vol.116, pages 1104–1109).

|  | $\Phi_B$ | $\Phi_{B \to A}$ | $k_T$ (sec$^{-1}$) | $\Phi_{F1}$ | $\tau_{F1}$ | $Q_{decom}$ |
|---|---|---|---|---|---|---|
| CM-X1 | 0.58 | 0.001 | $<1.6 \times 10^{-9}$ | 0.004 | 1.1 | 0.00001 |
| CM-X2 | 0.30 | 0.001 | $<1.6 \times 10^{-7}$ | No data | ~1 | <0.001 |
| Prior art | 0.6 | ~0.004 | $1.5 \times 10^{-5}$ | No data | 2 | 0.00014 |

$\Phi_B$ the quantum yield of the photocoloration A -> B in toluene for the light with the wavelength 405 nm
$\Phi_{B \to A}$ the quantum yield of the photodecoloration of the form B in toluene for the light with the wavelength 532 nm
$k_T$ rate constant of the back thermal reaction of the decoloration B -> A in polymethylmethacrylate at 22° C.
$\Phi_{F1}$ quantum yield of the fluorescence of the form B in toluene
$\tau_{F1}$ life time yield of the fluorescence of the form B in toluene
$Q_{decom}$ the quantum yield of the irreversible decomposition of the form B in polymethylmethacrylate at 22° C.

I claim:
1. Photochromic compounds of the following formula:

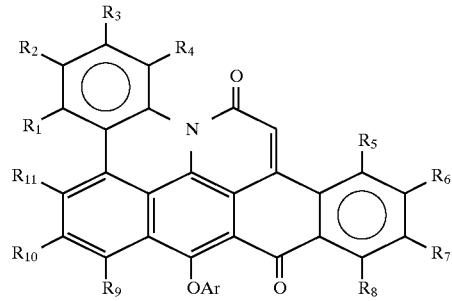

wherein $R_1$ to $R_{11}$ are independently selected and $R_1$ is selected from the group consisting of H, n-alkyl, isoalkyl, alkyne, alkene, benzyl, halogen, perfluoroalkyl, O-alkyl, O-alkylene, O-isoalkyl, O-alkyne, O-phenyl, S-alkyl, S-alkene, S-alkyne, S-phenyl or S-benzyl; $R_2$ is selected from the group consisting of H, n-alkyl, isoalkyl, alkyne, alkene, halogen, perfluoroalkyl, O-alkyl, O-alkylene, O-isoalkyl, O-alkyne, O-phenyl, O-benzyl, S-alkyl, S-alkene, S-alkyne, or S-phenyl; $R_3$ is selected from the group consisting of H, n-alkyl, isoalkyl, alkyne, alkene, halogen, perfluoroalkyl, O-alkyl, O-alkylene, O-isoalkyl, O-alkyne, O-phenyl, O-benzyl, S-alkyl, S-alkene, S-alkyne, S-phenyl or S-benzyl; $R_4$ is selected from the group consisting of H, alkyl, alkene, isoalkyl, alkyne, halogen or perfluoroalkyl; $R_5$ is selected from the group consisting of H, alkyl, alkene, isoalkyl, alkyne, halogen or perfluoroalkyl; $R_6$ is selected from the group consisting of H, n-alkyl, isoalkyl, alkene, alkyne, halogen, —OH, O-alkyl, O-alkylene, O-isoalkyl, O-alkyne, O-phenyl or O-benzyl, wherein the phenyl or benzyl group can have the following substituents: halogen, trifluoromethyl, alkyl, isoalkyl, —OH, O-alkyl, or O-isoalkyl; $R_7$ is selected from the group consisting of H, n-alkyl, isoalkyl, alkene, alkyne, halogen, —OH, O-alkyl, O-alkylene, O-isoalkyl, O-alkyne, O-phenyl or O-benzyl, wherein the phenyl or benzyl group can have the following substituents: halogen, trifluoromethyl, alkyl, isoalkyl, —OH, O-alkyl or O-isoalkyl; $R_8$ is selected from the group consisting of H, trifluoromethyl, halogen, methyl, ethyl, propyl, isopropyl, butyl or isobutyl; $R_9$ is selected from the group consisting of H, trifluoromethyl, halogen, methyl, ethyl, propyl, isopropyl, butyl or isobutyl; $R_{10}$ is selected from the group consisting of H, n-alkyl, isoalkyl, alkene, alkyne, halogen, —OH, O-alkyl, O-alkylene, O-isoalkyl, O-alkyne, O-phenyl or O-benzyl, wherein the phenyl or benzyl group can have the following substituents: halogen, trifluoromethyl, alkyl, isoalkyl, —OH, O-alkyl or O-isoalkyl; $R_{11}$ is selected from the group consisting of H, n-alkyl, isoalkyl, alkene, alkyne, halogen, —OH, O-alkyl, O-alkylene, O-isoalkyl, O-alkyne, O-phenyl or O-benzyl, wherein the phenyl or benzyl group can have the following substituents: halogen, trifluoromethyl, alkyl, isoalkyl, —OH, O-alkyl, or O-isoalkyl; and Ar is selected from the group consisting of phenyl,1-naphthyl, 2-naphthyl, alkyl substituted phenyl, halogen substituted phenyl, perfluoroalkyl, substituted phenyl, alkyl substituted-1-naphthyl, halogen substituted-1-naphthyl, perfluoroalkyl substituted 1-naphthyl, alkyl substituted-2-naphthyl, halogen substituted-2-naphthyl or perfluoroalkyl substituted-2-naphthyl.

2. Photochromic compounds of the following formula:

[Chemical structure showing a polycyclic compound with R₁ and R₂ substituents on one aromatic ring, a nitrogen-containing ring with C=O, a phenoxy (O-phenyl) group, and another C=O]

wherein $R_1$ and $R_2$ are independently selected and $R_1$ is selected from the group consisting of H, O-alkyl, and alkyl and $R_2$ is selected from the group consisting of H, n-$C_1$ to $C_{16}$ alkyl, O-n-$C_1$ to $C_{16}$ alkyl, halogen, vinyl, alkyl, isoalkyl O-isoalkyl and perfluoroalkyl.

3. The photochromic compound of claim 1 wherein $R_1$ is H and $R_2$ is n-$C_1$ to $C_{12}$ alkyl.

4. The photochromic compound of claim 2 wherein $R_2$ is butyl.

5. The photochromic compounds of claim 2 wherein $R_6$ is n-hexyl.

6. The photochromic compounds of claim 1 wherein $R_1$ is H and $R_2$ is O-alkyl of 1–12 carbons.

7. The photochromic compound of claim 5 wherein $R_2$ is O-methyl.

8. The photochromic compound of claim 1 wherein $R_1$ is H and $R_2$ is O-isoalkyl.

9. The photochromic compound of claim 7 wherein $R_2$ is selected from the group consisting of O-isopropyl, O-isobutyl, O-isopentyl, O-isohexyl, O-isoheptyl and O-isooctyl.

10. The photochromic compound of claim 1 wherein $R_1$ is H and $R_2$ is selected from vinyl and alkyl.

11. The photochromic compound of claim 9 wherein $R_2$ is vinyl.

12. The photochromic compound of claim 1 wherein $R_1$ is H and $R_2$ is halogen.

13. The photochromic compound of claim 11 wherein $R_1$ is chlorine.

14. The photochromic compounds of claim 1 wherein $R_1$ and $R_2$ are independently selected and $R_1$ selected from the group consisting of O-alkyl and H, and $R_2$ is perfluoro alkyl.

15. The photochromic compound of claim 13 wherein $R_1$ is selected from H and O-methyl and $R_2$ is trifluoromethyl.

16. A photochromic matrix comprising at least one photochromic compound of claim 1 distributed within a polymer matrix.

17. A photochromic matrix comprising at least one photochromic compound of claim 2 distributed within a polymer matrix.

18. A photochromic matrix comprising at least one compound of claim 5 distributed within a polymer matrix.

19. A photochromic matrix comprising at least one photochromic compound of claim 7 distributed within a polymer matrix.

20. A photochromic matrix comprising at least one photochromic compound of claim 9 distributed within a polymer matrix.

21. A photochromic matrix comprising at least one photochromic compound of claim 11 distributed within a polymer matrix.

22. A photochromic matrix comprising at least one photochromic compound of claim 13 distributed within a polymer matrix.

23. The photochromic matrix of claim 15 wherein the polymer is selected from polyacrylates, polymethyl acrylates, polymethyl methacrylates, polystyrene and polyesters.

24. The photochromic matrix of claim 23 wherein the polymer is polymethyl methacrylate.

* * * * *